United States Patent [19]

Milgrom

[11] 4,427,477
[45] Jan. 24, 1984

[54] METHOD FOR MAKING A LIPPED VAGINAL CONTRACEPTIVE DIAPHRAGM

[75] Inventor: Hymen Milgrom, Chicago, Ill.

[73] Assignee: Milex Products, Incorporated, Chicago, Ill.

[21] Appl. No.: 474,533

[22] Filed: Mar. 11, 1983

[51] Int. Cl.³ .............................................. A61F 5/46
[52] U.S. Cl. .................................. 156/213; 128/127; 156/245; 156/293; 156/307.1
[58] Field of Search ...................... 128/127, 130, 131; 156/69, 213, 245, 293, 307.1, 285

[56] References Cited

U.S. PATENT DOCUMENTS

| | | | |
|---|---|---|---|
| 2,859,061 | 11/1958 | Reid | 156/213 |
| 3,036,570 | 5/1962 | Milgrom et al. | 128/127 |
| 3,060,931 | 10/1962 | Clark | 128/127 |
| 3,169,522 | 2/1965 | Monett | 128/127 |

*Primary Examiner*—Jerome W. Massie

*Attorney, Agent, or Firm*—Russell E. Hattis; Stephen R. Arnold

[57] ABSTRACT

A method for making a cervical contraceptive diaphragm provides for fabricating the entire dome assembly in a separate step, thereafter inserting a toroidal spring within a toroidal chamber pre-formed in a flange affixed to the base of the dome structure, the spring being sealed in by a separate sealing process preferably by a thin filament of vulcanizable rubber laid along the flange away from the spring. Local heating of the filament to cure it and seal the flange about the spring provides for a spring not interpenetrated by liquid elastomer during the curing process, resulting in a free floating spring. The method allows the fabrication of structures employing relatively stiff springs of limited radial compliance, so that the diaphragm may be removed from the first forming mold with minimum loss arising from tearing of the lip.

7 Claims, 8 Drawing Figures

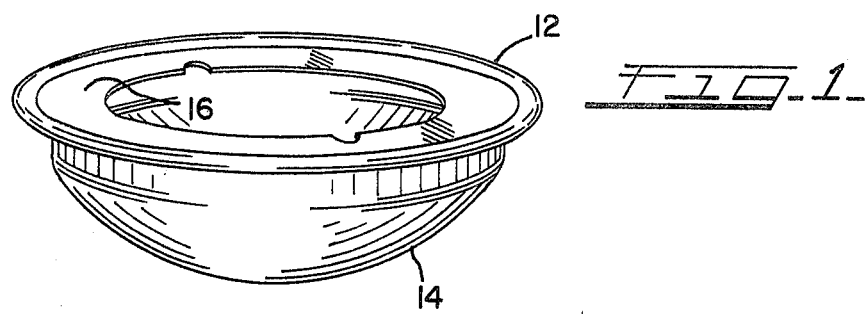
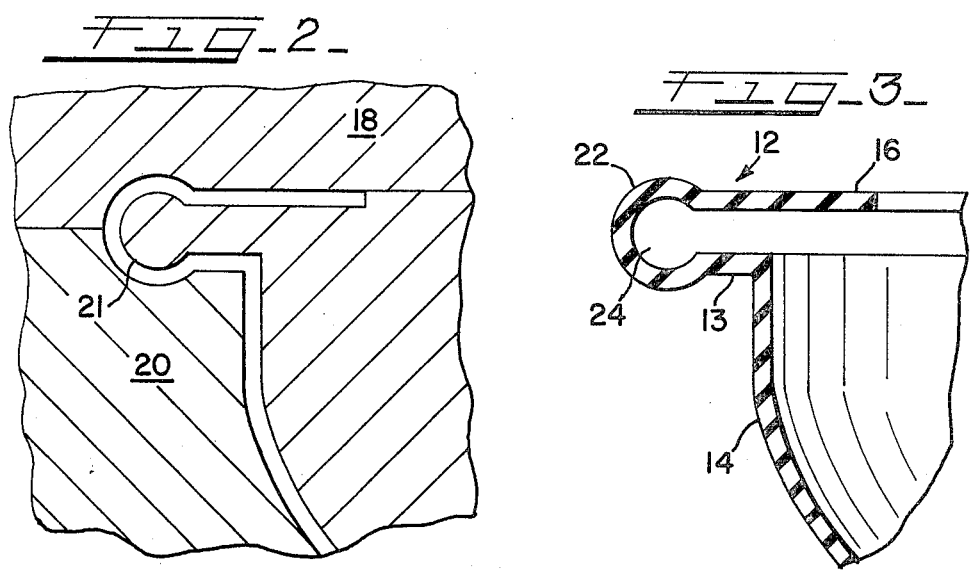
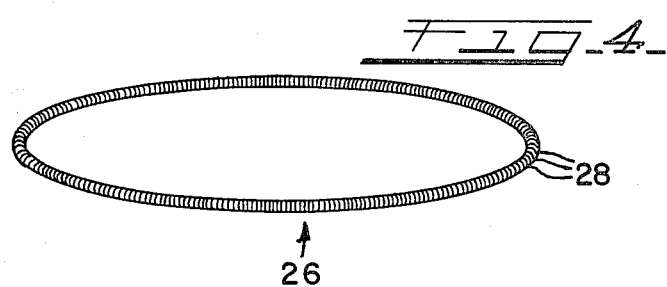

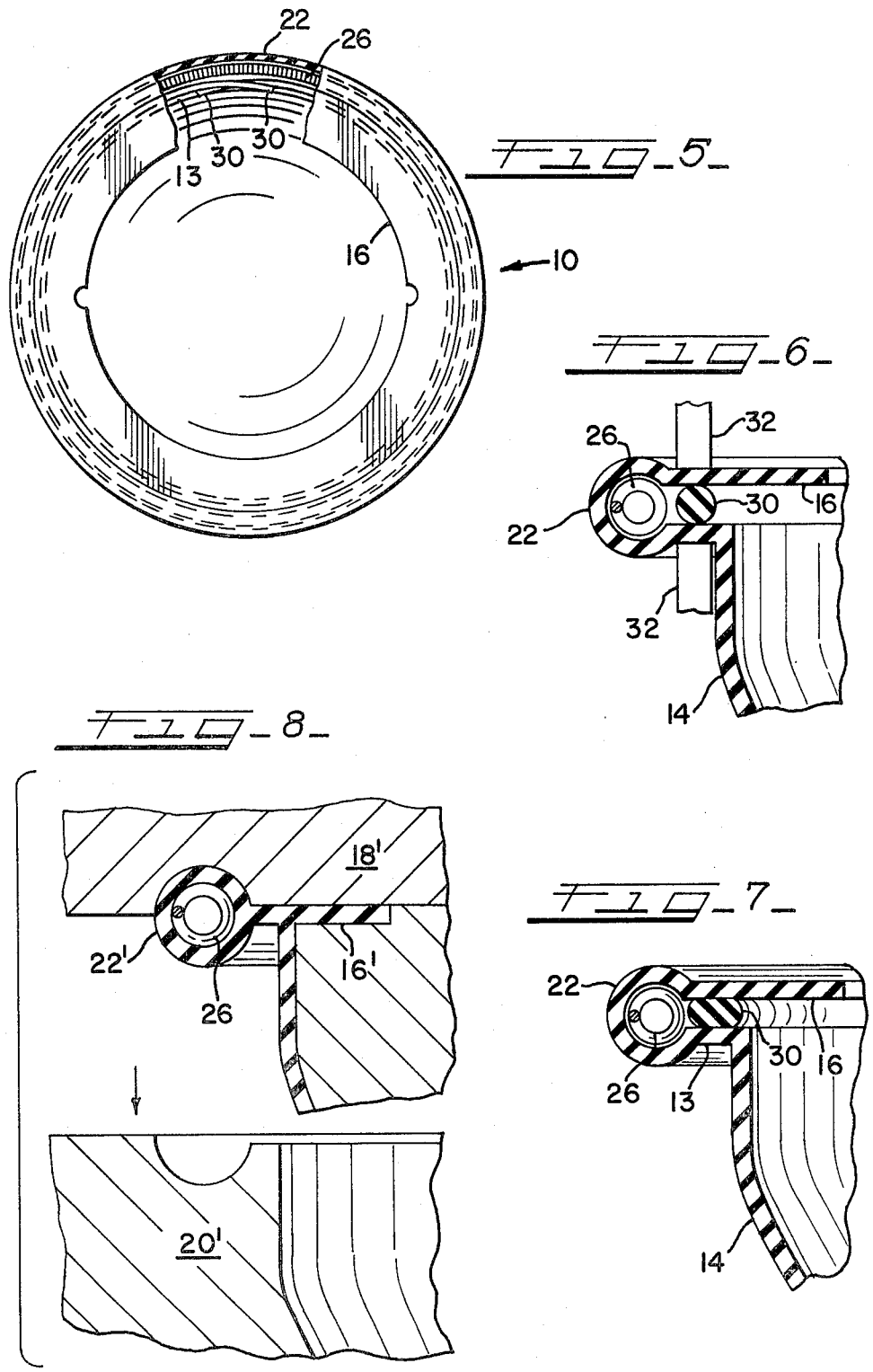

METHOD FOR MAKING A LIPPED VAGINAL CONTRACEPTIVE DIAPHRAGM

TECHNICAL FIELD OF INVENTION

The technical field of the invention is manufacturing methods for contraceptive devices, in particular vaginal diaphragms (pessaries).

BACKGROUND OF THE INVENTION

U.S. Pat. No. 3,036,570 issued to H. T. Milgrom and W. T. Hewboski discloses a vaginal contraceptive diaphragm (pessary) having an integral inwardly projecting lip to provide increased retention thereof. An embedded toroidally wound spring peripherally disposed within a flange surrounding a central dome-shaped portion provides the principal retentive force, the spring being integrally molded to the flange during the manufacturing process, using conventional pressure molding techniques. The dome-like portion with an integral flange is first manufactured in a separate step by pressure molding, whereupon the spring is laid over an annular portion of the flange, and the second inwardly extending lip portion is formed therearound in a second molding operation wherein the lip is formed integrally attached to the flange of the diaphragm body, with the spring trapped there between.

This manufacturing process frequently results in the spring being carried completely to the edge of the structure because of molding pressures, resulting in a spring substantially off center, and close to, if not actually penetrating, the outer wall of the flange. Since the spring portion is routinely flexed in insertion, a possibility exists that a thin flange wall in the vicinity of the spring can result in a protruding spring, resulting in irritation to the user. Such defects are frequently observed during the manufacturing process, resulting in a substantial number of manufacturing rejects. Additionally, as will subsequently be discussed, this integral formation method leads to a substantial problem in extracting the finished diaphragm assembly from the injection mold, because of topological problems presented by the inwardly extending lip and spring rigidity.

Another difficulty arises from the fact that the spring has a specific heat substantially different from the elastomer from which the lip and flange are formed, with the result that it is difficult to get an adequate and uniform heating of the elastomer around the spring to provide adequate and uniform curing without causing local overcuring and concomitant embrittlement. Moreover, since the spring is embedded in the elastomer and has its windings interpenetrated by the elastomer during the molding process, the result is that the resulting structures so produced have quite variable spring tension properties, owing to the above mentioned curing problems, as well as the fact that the interpenetration by the elastomer is not subject to close control. A further feature of such a structure, wherein the spring is captively embedded in the flange, lies in its rigidity during insertion by the user, since the elastomer is not free to rotate at all about the toroidal spring. This is can be a source of discomfort.

Thus, it has been considered desirable that an improved manufacturing process be developed that would provide a more controllably curable assembly wherein no substantial lateral displacement of the spring occurs, with the associated danger of producing an unacceptably thin outer wall. A process that would yield a less rigid structure would also be desirable.

SUMMARY OF INVENTION

According to the invention a vaginal contraceptive diaphragm is formed by first forming a dome-like shield structure having a peripheral flange and having integrally formed at the same time therewith a folded back membrane forming an interior sealing lip, the interior region of the periphery of the assembly being formed in the shape of an annular toroidal chamber. The dome shield is formed as a single unit by molding techniques wherein it is partially cured to a "set" condition. The dome shield is then removed from the mold, a toroidal spring is inserted into the annular toroidal chamber, and a loop of uncured elastomer is placed on the flange substantially coplanarly with the toroidal spring and disposed inwardly therefrom. Local heat curing is then applied to cure the loop and fuse it to the flange and the portion of the inwardly extending lip immediately in contact with it, thereby sealing the spring within the toroidal chamber. Since the loop does not contact the spring during the local curing process, the spring is thus held loosely captive in the toroidal chamber. The result is a well centered sealed retention spring, having no penetration of the windings thereof by any flowing elastomer, thereby providing the previously mentioned desirable uniformity of tension. Since the spring does not contact the region being cured during the sealing process, a substantially improved control over uniformity of curing is achieved. Thin walls and possible protrusion of the spring therethrough are completely eliminated, and the free floating spring allows a more comfortable rolling insertion of the finished device.

Other advantages and features of the invention will become apparent upon making reference to the description to follow, the drawings, and the claims.

DESCRIPTION OF DRAWINGS

FIG. 1 is a perspective view of a formed dome shield made of elastomer material;

FIG. 2 is a partial cross section view of a mold used to produce the dome shield of FIG. 1, showing a toroidal spring retention chamber.

FIG. 3 is a partial cross section view of the edge region of the dome shield of FIG. 1, again showing the toroidal spring retention chamber disposed outboard of the central element of the dome and attached to a lip and supporting shelf;

FIG. 4 is a perspective view of a spiral wrapped toroidal spring, showing the windings thereof;

FIG. 5 is a cross sectional plan view through the toroidal chamber of FIG. 3 showing the spring of FIG. 4 in place, with an elastomeric filament disposed inwardly therefrom with overlapping ends preparatory to local curing to seal the shelf of FIG. 3 to the lip positioned thereabove;

FIG. 6 is a partial cross section view of the flange portion of the dome shield of FIG. 1 with the spring of FIG. 4 inserted, showing the position of the elastomeric filament shown in FIG. 5 mounted between two ring shaped heater elements applied for local fusion and curing of the filament; and FIG. 7 is a view similar to FIG. 6 after the curing of the filament, showing the sealing action trapping the toroidal spring within the toroidal chamber.

FIG. 8 is a cross section view of the prior art manufacturing method, showing the mold parts withdrawn just prior to removal of the pessary.

DESCRIPTION OF THE INVENTION

The subject matter of the present disclosure is an improved method for forming a contraceptive vaginal diaphragm shield of the type shown in FIG. 1 having a thin walled dome portion 14 and an outwardly extending flange portion 12 containing a toroidally disposed interior toroidal spring (not shown-See FIG. 4), the shield further having an inwardly extending lip 16 in the form of a generally planar membrane, the lip providing for increased retention according to the teaching of U.S. Pat. No. 3,036,570.

The dome shield of FIG. 2 is produced by molding techniques using a two part mold consisting of upper element 18 and lower element 20 shown in FIG. 2. A toroidal ring 21 outwardly disposed from and connected to the central convex downwardly extending portion of upper mold portion 18 serves to define an interior toroidal annular chamber when the passages between the two molds are filled by fluid elastomer via molding passages (not shown). Representative values, using natural rubber for the elastomer, for the first cure to a 90% "set" condition are typically 3.5 minutes at 350 degrees Fahrenheit.

The resulting structure when finished is in the form shown in FIG. 1, having a radial flange portion 12 (FIG. 3) configured as shown. The structure has a peripheral toroidal chamber 24 defined by a toroidal wall 22, the chamber supported outboard of the dome portion 14 by a shelf 13, the lip 16 extending radially inward from the upper interior portion of the toroidal wall 22. By inspection of FIGS. 2 and 3, it will be appreciated that, owing to the flexibility of the structure, the dome shield 10 is readily removed from the upper mold 18 after curing and mold separation by a simple radial and pull-away stretching operation. The advantage of such a feature will be discussed subsequently.

Next, a toroidal spring 26 (FIG. 4) consisting of helical spring wraps 28, is inserted into the toroidal chamber 24 as shown. To seal the structure together an uncured elastomer filament 30, most preferably in the form of a single filament placed with the ends overlapping as shown in FIG. 5, is disposed upon a joining region on the shelf portion 13 of the flange, the assembly being placed between two annular heating rings 32—32 as shown in FIG. 6.

Upon application of heat to the heating rings 32—32, the uncured elastomer 30 flows to seal the lip 16 and the shelf 13 of FIG. 6 together, the resulting structure as being shown in FIG. 7. A typical curing schedule is one minute at 200 degrees Fahrenheit, resulting in sufficient structural integrity to allow subsequent handling. Although a simple cementing operation would appear to be adequate for this step, experience has shown that unreliable seals result. However, so that the broadest aspect of the present invention will still apply should there be found a convenient effective adhesive having suitable non-toxic properties, the broadest aspect of the invention envisions sealing the spring means by adhesively securing said lip to said flange along the margin of said annular chamber to seal the spring means therein. The adhesive material is preferably curable adhesive material which is partially cured during the sealing step. Then both the curable elastomeric diaphragm body and the partially cured adhesive can be subsequently simultaneously completed cured by subjecting the same to a suitable curing environment.

It will be noted that the toroidal spring 26 is now sealed withing the chamber 24 in a free floating condition, the elastomeric filament 30 being of such quantity and dimension as not to flow into the chamber to bond to the spring. Final curing of the entire assembly is then carried out by high pressure high temperature steam, most preferably in an autoclave at 15 p.s.i for 20 minutes.

Conventional fabrication techniques for such structures involve forming the dome shield and flange first, laying the spring thereon, and then molding and vulcanizing the remainder of the lip structure around and in contact with the spring. FIG. 8 illustrates the final stage of such a method, showing the mold part 18' and 20' withdrawn, with the assembly still held captively secured to the top part 18'. A variety of disadvantages arising from this process are eliminated by the present method as will be discussed.

A variety of advantages result from the present method:

First, by providing for a loosely captive spring, a measure of rotation of the outer wall 22 is allowed during insertion by the user, thereby removing a measure of discomfort frequently attendant thereto.

Second, since the specific heat of the spring and the elastomer are substantially different, the second molding and vulcanizing operation is difficult to control throughout the flange structure, often resulting in sealing failure by undercuring or overcuring. By physically isolating the spring mass from the joining region, and by locally sealing this region, this problem is eliminated.

Third, the conventional method inherently causes the elastomer to interpenetrate the spring windings, thereby affecting spring regidity. Since the subsequent curing is, as stated above, quite variable in its properties, the resulting spring stiffness is similarly variable and difficult to control. This problem also is eliminated.

Fourth, as mentioned in the Background of the Invention, the second molding process frequently displaces the spring laterally, producing an unacceptably thin wall or a local failure to seal around the spring. By fabricating the retaining walls first, this problem is eliminated.

Finally, such springs 21 as shown in FIG. 4 have only a very limited radial stretching capacity. Thus, with reference to FIG. 8, it will be appreciated that such a diaphragm structure with a lip configuration 16' poses certain basic problems with respect to the molding process. Here instead of providing for a toroidal ring 21 defining the spring chamber 24, such a stiffened spring itself is fused into place by conventional techniques. It has proven to be extremely difficult to achieve separation of the structure so formed from the upper half mold portion 18', because only a limited radial outward stretching can be imparted to the spring to pull it free from its captive position in the mold. The result is that conventional fabrication techniques are more time consuming, and frequently result in spoilage during manufacture by tearing of the flange during the removal operation. Thus, the previously recited process not only produces a more desirable product, but substantially improves production yield for lip carrying diaphragms.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to a particular embodiment disclosed as the best mode contemplated for carrying out the invention, but that the invention will include all embodiments falling within the scope of the appended claims.

I claim:

1. A method for making a cervical contraceptive diaphragm assembly comprising the steps of:

forming an elastomeric vaginal diaphragm body, said body configured with a central shell-like dome having an outwardly extending flange peripherally attached thereto, said body having a annularly shaped generally planar lip joined at the outer periphery thereof at all points therealong to the outer peripheral edge of said flange to form an annular chamber between said flange and an outer annular portion of said lip, said lip being configured to extend generally planarly inwardly beyond the juncture of said flange and said dome;

providing a toroidally configured spring means and disposing same to lie completely within said annular chamber and proximate to the outer wall thereof, so as to leave an interior annular portion of said flange and an opposing annular portion of said lip facing each other to form an annular joining region along what is to be the inner margin of said annular chamber;

sealing said lip to said flange along the margin of said annular chamber so as to seal the spring means therein.

2. The method of claim 1 wherein said elastomeric diaphragm body is initially partially cured to said setting condition, and said sealing step includes sealing said lip to said flange through a body of curable material added along said margin, and then partially curing the same, and then curing said assembly to a substantially cured condition.

3. The method of claim 2 wherein said body of curable material is an elastomeric filament placed along said margin of the chamber between said lip and flange.

4. The method of claim 1 wherein said annular chamber is configured as a thin-walled toroid approximating the dimensions of said toroidal spring means.

5. The method of claim 3 wherein said elastomeric filament is a linear flexible filament placed on said flange along said margin of the annular chamber with the ends of said filament disposed in overlapping contact to form a loop thereof.

6. The method of claim 2 wherein said step of at least partially curing said joining region comprises local heating of substantially only the joining region between said lip and flange.

7. The method of claim 6 wherein said step of curing said assembly to a substantially completely cured condition comprises treating said assembly at elevated temperatures in the presence of water vapor.

* * * * *